US00PP13459P2

(12) United States Plant Patent
Yates

(10) Patent No.: US PP13,459 P2
(45) Date of Patent: Jan. 7, 2003

(54) ANTIRRHINUM PLANT NAMED 'YAPEAR'

(76) Inventor: Frederic Yates, Poplar Nursery, Holmes Chapel Rd., Somerford, Congleton, Cheshire (GB), CW12 4FP ( * ) Notice: Subject to any disclaimer, the term of this patent is extended or adjusted under 35 U.S.C. 154(b) by 103 days.

(21) Appl. No.: 09/689,325

(22) Filed: Oct. 12, 2000

(51) Int. Cl.[7] ..... A01H 5/00

(52) U.S. Cl. ..... Plt./322

(58) Field of Search ..... Plt./322

*Primary Examiner*—Bruce R. Campell
*Assistant Examiner*—Michelle Kizilkaya
(74) *Attorney, Agent, or Firm*—Mark P. Bourgeois

(57) ABSTRACT

A new cultivar of Antirrhinum named 'Yapear' that is characterized by a compact habit, profuse clear-white outward facing flowers, and large consistently sized leaves.

3 Drawing Sheets

CROSS-REFERENCES TO RELATED APPLICATIONS

This application is co-pending with another application entitled Antirrhinum Plant named 'Yahit', having the same inventor as the present invention, and is related to the following previously filed applications entitled Antirrhinum Plants Named 'Yablu' (Ser. No. 09/520,231), 'Yarprim' (Ser. No. 09/520,227), 'Yapeep' (Ser. No. 09/520,230), 'Yarob' (Ser. No. 09/520,228), and 'Yalil' (Ser. No. 09/520,229). 'Yablu', 'Yaprim', 'Yapeep', 'Yarob', and 'Yalil' are all patent pending and were all filed on the same date that of Mar. 7, 2000.

BACKGROUND OF THE INVENTION

The present invention relates to a new and distinct cultivar of Snapdragon, known botanically as an Antirrhinum of hybrid origin and referred to hereinafter by the cultivar name 'Yapear'.

The New Snapdragon was selected by the inventor from his breeding program in a cultivated area of Congleton, Chesire, England. The objective of the program is to select new cultivars of Snapdragons that have a trailing growth habit with an outward presentation of the flowers in a range of flower colors. Seedlings were first crossed in the summer of 1997 by the inventor in Congleton, Chesire, England. The parents are unintroduced Antirrhinums of hybrid origin from the inventors breeding program. 'Yahit' originated from a seed bed containing open pollinated hybrids of *Antirrhinum gluutinosum×majus* (not patented) and *Antirrhinum braun-blanquettii* (not patented). The exact parents are unknown. The hybrid seedling 'Yapear' was selected by the inventor in May 1998.

The following characteristics are unique and distinguish the new invention from all other varieties. 'Yapear' has a compact form, exhibiting numerous clear-white flowers with an outward aspect and large consistently sized leaves. The closest comparison plants are *Antirrhinum* 'Avalanche' (not patented) and Antirrhinum 'Lawhi' (U.S. Plant Pat. No. 10,006). Compared to 'Avalanche', 'Yaper' is more compact with more flowers per flowering spike, more white in the flower color, and slightly larger, more evenly shaped leaves. 'Yapear' differs from 'Lawhi' by exhibiting a cascading habit with all flowers facing outward.

'Yapear' is distinguished from *Antirrhinum gluutinosum× majus* and *Antirrhinum braun-blanquetti* by whiter flowers, more silver colored foliage and more vigorous growth.

The first asexual propagation was conducted in June of 1999 by the inventor in Congleton, Chesire, England. Three successions of cuttings were taken with varietal stability insured. The unique characteristics of 'Yapear' have been found to be stable in successive generations.

SUMMARY OF THE INVENTION

The following traits have been repeatedly observed and represent the characteristics of the new cultivar. These attributes in combination distinguish this cultivar from other commercial varieties known to the inventor. 'Yapear' is compact in form exhibiting a profuse display of clear-white flowers with a consistently outward presentation, and large consistently sized leaves. 'Yapear' has not been tested under all possible conditions and phenotypic differences may be observed with variations in environmental, climatic, and cultural conditions.

BRIEF DESCRIPTION OF THE DRAWINGS

The accompanying color photographs illustrate the overall appearance of the new cultivar 'Yapear'.

Sheet 1 shows the foliage, flower color, flower presentation, and compact habit of 'Yapear'.

Sheet 2 is a close-up view of the 'Yapear' flower.

Sheet 3 illustrates the stem, foliage and flower of 'Yapear'. All photographs are taken of 6 month old plants grown in one-gallon containers under greenhouse conditions in Encinitas Calif.

The prints are made using conventional photographic techniques and although foliage color may appear different from actual colors due to light reflectance, they are as accurate as possible by conventional photography.

BOTANICAL DESCRIPTION OF THE PLANT

The following is a detailed description of a 6 month old plant of the new cultivar as grown in a one-gallon container under greenhouse conditions in Encinitas, Calif. Phenotypic differences may be observed with variations in environmental, climatic, and cultural conditions. The color determinations are in accordance with The Royal Horticultural Society except where general color terms of ordinary dictionary significance are used.

Botanical classification: *Antirrhinum glutinosum×majus* 'Yapear'.
Parentage:
*Seed parent.*—Unknown Antirrhinum hybrid.
*Pollen parent.*—Unknown Antirrhinum hybrid.
Common name: Snapdragon.
Use: Hanging basket or patio plant.
Parentage: Both parents are unintroduced Antirrhinum hybrids from the inventors breeding program.
Propagation: Tip cuttings.
Growing conditions: Grow cuttings, and young plants cool, at approximately 8–12 degrees Centigrade, and pinch before main growth starts.
Type: Vegetatively propagated annual.
Branching habit: Freely branching.
Root system: Fibrous.
Time to initiate roots: 10 days at 20 degrees Celsius.
Height and width: 30–35 cm high and 35–40 cm wide.
Diseases and pests: Potential for fungal disease of roots.
Special needs: Benefits from incorporated fungicide to prevent root disease.
Plant habit: Cascading.
Seasonal interest: Spring, summer and fall floral display.
Hardiness: −10 degrees Centigrade.
Stem shape: Cylindrical.
Stem color: 138B.
Stem size: 20 cm in length by 2 mm in diameter.
Internode length: 1.5 ñ2.5 cm between nodes.
Stem surface: Woolly and tomentose.
Stem texture: Flexible and velvety.
Foliage:
*Leaf arrangement.*—Opposite.
*Leaf division.*—Simple.
*Shape.*—Oval.
*Base.*—Attenuate.
*Apex.*—Rounded.
*Venation.*—Prominent mid-vein.
*Vein color* (*upper surface*).—138B.
*Vein color* (*lower surface*).—137C.
*Margins.*—Entire.
*Leaf surface* (*upper*).—Heavily tomentose and woolly.
*Leaf surface* (*lower*).—Heavily tomentose and woolly.
*Leaf color* (*upper surface*).—139A.
*Leaf color* (*lower surface*).—137B.
*Length.*—1.5 cm long.
*Width.*—1 cm wide.
*Petiole length.*—6 mm long.
*Petiole width.*—1 mm wide.
*Petiole color.*—138B.
Flower buds:
*Bud dimension.*—1.5 cm in length, 1.0 cm in width.
*Bud color.*—145D.
Flower:
*Type.*—Racemiform with leafy terminal racemes.
*Form.*—Bilabiate.
*Symmetry.*—Zygomorphic.
*Margins.*—Entire.
*Texture.*—Glabrous.
*Flower color* (*opening*).—145C, D.
*Unique markings* (*mature flower*).—Subtle purple-violet veins on upper petal and corolla tube.
*Vein color* (*mature flower*).—80A.
*Overall color of anterior lobe or lower petal* (*mature flower*).—155D.
*Overall color of banner or upper petal* (*mature flower*).—155D.
*Palate color* (*mature flower*).—155C.
*Overall color of corolla tube* (*mature flower*).—155D.
*Fragrance.*—Faint perfume scent.
*Flowering season.*—Spring, summer and fall.
*Time to produce flowers.* 12 to 16 weeks.
*Flowering time.*—Diurnal.
*Lastingness.*—7 to 10 days.
*Aspect.*—Flowers facing outward.
*Height.*—2.5 cm high.
*Length.*—2.8 cm long.
*Peduncle length.*—5 cm long.
*Peduncle width.*—2 mm in diameter.
*Petal number.*—Two petals.
*Petal length.*—2.5 cm long.
*Petal width.*—1.5 cm wide.
*Fused or unfused.*—Petals are fused.
*Petal surface.*—Glabrous.
*Calyx size.*—75 cm long and 0.2 cm wide.
*Number of sepals.*—Aposepalous with five sepals.
*Sepal color.*—137–138D.
*Sepal surface.*—Stipitate glandular.
Reproductive organs:
*Stamens.*—4.
*Stamen dimensions.*—2.5 cm in length, 1 mm in width.
*Anther attachment.*—Dorasfixed.
*Anther dimensions.*—2 mm in length, 1 mm in width.
*Anther color.*—13A
*Pollen color.*—15A.
*Pollen amount.*—Moderate.
*Staminode.*—1.
*Pistil.*—1.
*Pistil dimensions.*—15 mm in length, 1 mm in width.
*Pistil color.*—155B.
*Style dimensions.*—3 mm in length, 1 mm in width.
*Style color.*—145A.
*Stigma dimensions.*—3 mm in length, 3 mm in width.
*Stigma color.*—144B.
*Ovary shape.*—Globose.
*Ovary position.*—Superior.
*Ovary dimensions.*—3 mm in length, 3 mm in width.
*Ovary color.*—145A.
Seed:
*Seed shape.*—Ovoid.
*Seed dimensions.*—1.5 mm in length, 0.75 mm in width.
*Seed color.*—Black.

I claim:

1. A new and distinct cultivar of Antirrhinum plant named 'Yapear' as described and illustrated.

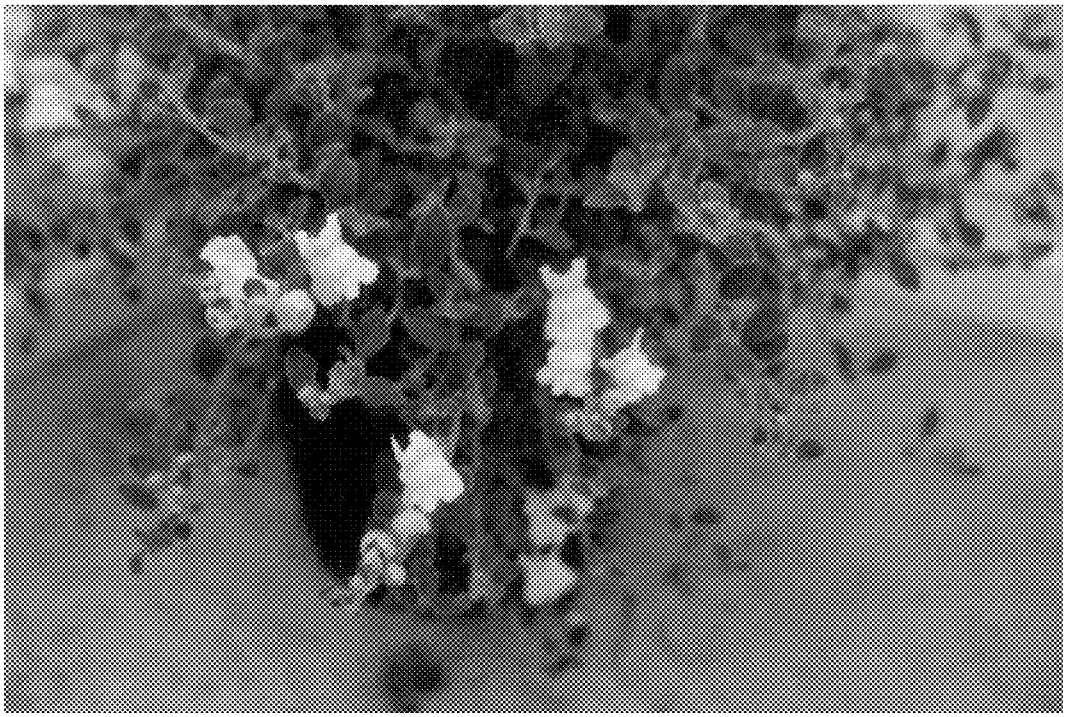

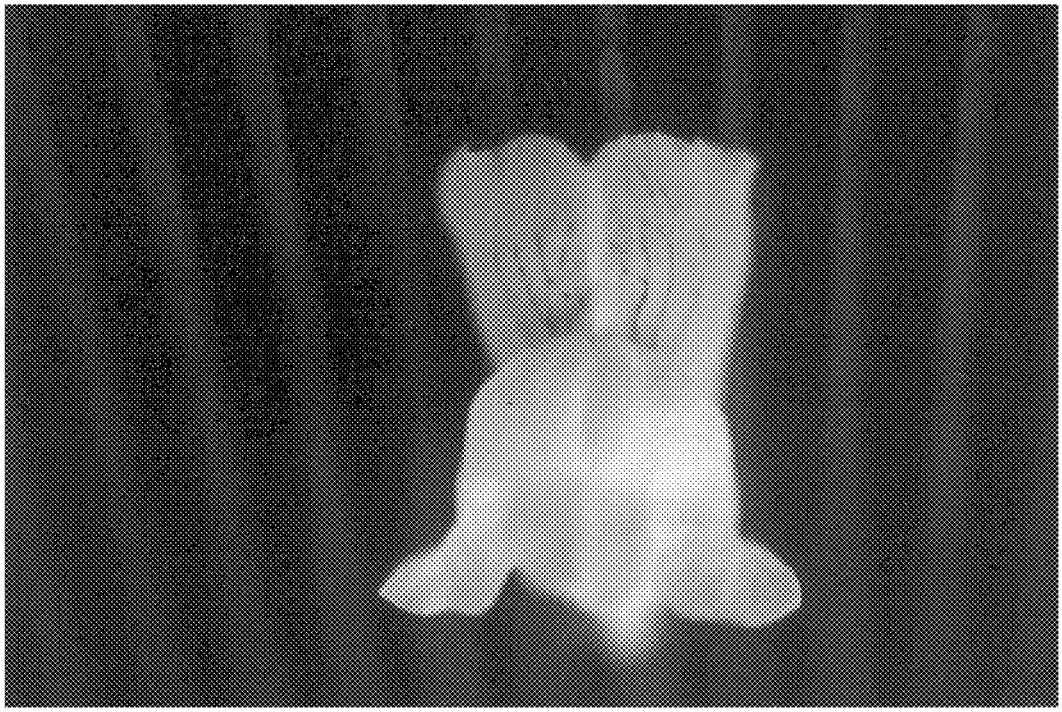

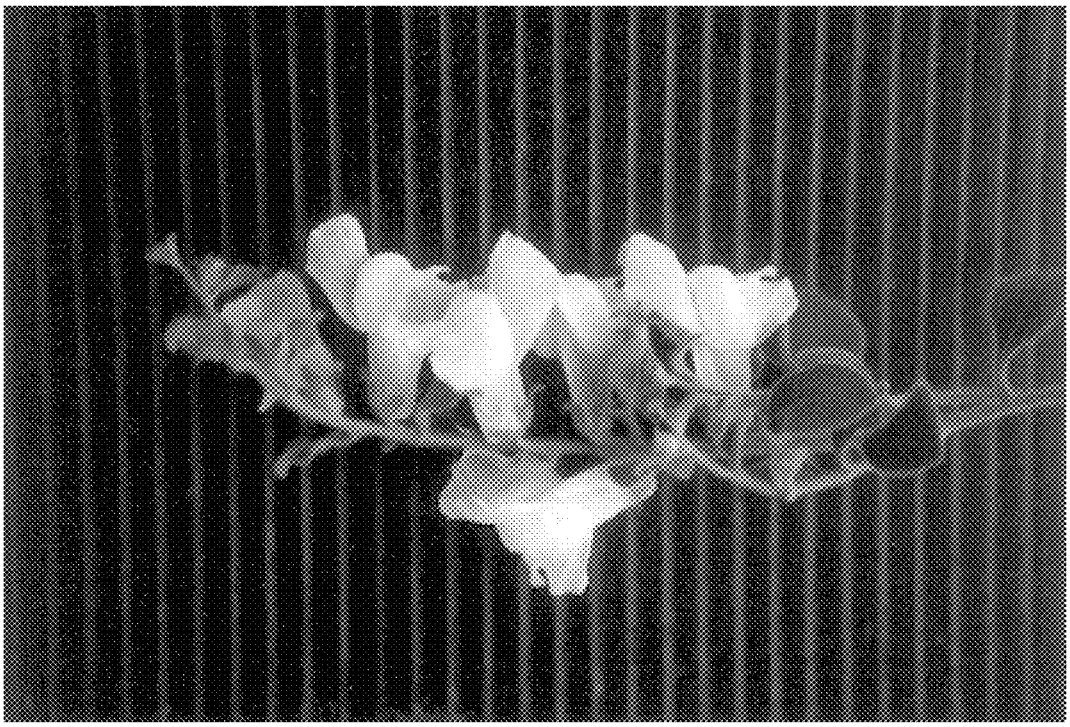

* * * * *